United States Patent [19]
Zelman

[11] Patent Number: 4,825,865
[45] Date of Patent: May 2, 1989

[54] APPARATUS AND METHOD FOR EXTRACTING CATARACT TISSUE

[76] Inventor: Jerry Zelman, c/o International Medical Building, 960 Arthur Godfrey Rd., Ste. 401, Miami Beach, Fla. 33140

[21] Appl. No.: 44,544

[22] Filed: May 1, 1987

[51] Int. Cl.$^4$ .............................................. A61B 17/00
[52] U.S. Cl. .................................. 128/303.1; 604/27; 604/266
[58] Field of Search ...................... 604/20, 27, 28, 43, 604/266-268, 902, 22, 30, 35; 126/303.1, 395

[56] References Cited

U.S. PATENT DOCUMENTS

| | | | |
|---|---|---|---|
| 1,112,982 | 10/1914 | Conine | 604/267 |
| 2,137,635 | 11/1938 | Tyler | 604/267 |
| 3,352,303 | 11/1967 | Delaney | 604/22 |
| 3,693,613 | 9/1972 | Kelman | 604/22 |
| 3,942,519 | 3/1976 | Shock | 128/303.1 |
| 3,958,573 | 5/1976 | Wiley | 604/267 |
| 3,971,382 | 7/1976 | Krasnov . | |
| 3,982,541 | 9/1976 | L'Esperance | 604/20 |
| 4,011,869 | 3/1977 | Seiler, Jr. | 604/267 |
| 4,223,676 | 9/1980 | Wuchinich | 604/22 |
| 4,445,517 | 5/1984 | Feild | 604/35 |
| 4,516,398 | 5/1985 | Wuchinich | 604/22 |
| 4,520,816 | 6/1985 | Schachar et al. | 128/303.1 |
| 4,522,206 | 6/1985 | Whipple et al. | 128/305 |
| 4,633,866 | 1/1987 | Peyman et al. | 128/303.1 |
| 4,644,951 | 2/1987 | Bays | 604/22 |
| 4,655,743 | 4/1987 | Hyde | 604/22 |
| 4,678,459 | 7/1987 | Owik et al. | 604/22 |
| 4,694,828 | 9/1987 | Eichenbaum | 128/303.1 |
| 4,735,604 | 4/1988 | Watmough et al. | 604/35 |

FOREIGN PATENT DOCUMENTS 175096  3/1986  European Pat. Off. .............. 604/33

OTHER PUBLICATIONS

Am Intra Ocular Implant Soc. Journal, vol. 11, Jan. 1985, pp. 33-34, Chambles.
Journal of Cataract Refract Surg, vol. 13, May 1987, pp. 287-289, Zelman, J.

Primary Examiner—Lee S. Cohen
Assistant Examiner—David Shay
Attorney, Agent, or Firm—Cushman, Darby & Cushman

[57] ABSTRACT

Apparatus and method for extracting cataract tissue in which the cataract is first softened by focusing laser radiation thereon and subsequently a tube inserted through an incision to a position adjacent the cataract. An irrigating liquid is supplied through one portion of the tube and the liquid and cataract fragments removed via an aspirating opening adjacent the tube opening. Fragments which do not readily pass through the aspirating opening are dislodged by vibration or broken up by a paddle like member pivotally mounted adjacent the aspirating opening to engage the fragment and apply a force to break up the same.

19 Claims, 2 Drawing Sheets

APPARATUS AND METHOD FOR EXTRACTING CATARACT TISSUE

BACKGROUND OF THE INVENTION

The invention relates to an apparatus and method for extracting cataract tissue.

Every eye is divided into an anterior and posterior chamber by a normally transparent lens which focuses light onto the retina at the back of the posterior chamber. When the lens becomes cloudy for any of a variety of reasons, sight is impaired and the cloudy lens must be removed. Following removal of the lens, an intraocular lens (IOL) implant can be placed in the posterior chamber or thick glasses or contact lenses used to focus the light properly onto the retina.

A number of techniques are now in use for removing the cloudy cataract lens. In all these techniques a surgical tool is inserted into the eye through a small incision. Phacoemulsification is a recently developed technique which is being used more and more frequently. A small incision is made in the surface of the eye and a probe in the form of a rigid or semi-rigid tube inserted. This tube defines two internal paths-one for supplying an aspirating liquid, typically water, to the interior of the eye and a second to which a vacuum is connected for sucking out fragments of the cataract tissue and the aspirating liquid. Ultrasonic vibration is applied to the tube after the sharpened end is inserted by the surgeon into the cataract tissue. The ultrasonic vibration breaks up the cataract tissue which is aspirated together with the irrigating liquid.

One advantage of phacoemulsification is that the incision in the eye can be smaller than with other techniques. A smaller incision stabilizes the refractive error sooner and reduces the amount of induced post operative astigmatism. Of course that advantage is lost if the incision must be lengthened to insert the IOL. However, the present development of small incision intraocular lenses and the future possibility of in sito formation of lenses by injection of polymer into the intact capsular bag make phacoemulsification particularly attractive since with these techniques the incision need not be increased beyond the initial 2.5–3.5 millimeters required for phacoemulsification.

One difficulty with phacoemulsification is that considerable problems are often encountered in mastering the skills needed to perform the procedure safely. Further, occasional difficulties arise in removing all of the cataract tissue. In addition the sharp point of the probe can inadvertently damage delicate eye tissues.

Laser radiation has for the past several years been used to ablate various tissues within the eye. For example, the use of a ND:YAG laser (hereinafter referred to by the more common term, YAG laser) to remove abnormal and normal tissue has been explored, for example, see the patent to Krasnov, U.S. Pat. No. 3,971,382; U.S. application Ser. No. 702,569 filed Feb. 19, 1985; and an article by William Steven Chambles entitled *Neodymium: YAG Laser Anterior Capsulotomy And A Possible New Application,* (AM Intra-Ocular Implant Society Journal, Vol. 11, January 1985). It has generally been recognized that laser radiation, particularly from a YAG laser, will soften cataract tissue.

However, one of the difficulties with the use of laser radiation to soften cataract tissue is that the fragments of the tissue are often too large or otherwise dimensioned to pass readily through an aspirating opening in a probe such as used in phacoemulsification. In order to avoid making the incision more than the desired 2.5–3.5 millimeters, the aspirating opening must necessarily be quite small and the dimensions of the path within the probe to the vacuum source similarly restricted. For that and other reasons, the use of laser radiation to soften cataracts for subsequent aspiration has not been practical as a standard surgical procedure.

SUMMARY OF THE INVENTION

The present invention relates to a unique apparatus and method which resolves the above-noted problem and makes practical the use of laser radiation to soften and eventually fragment cataract tissue which can then be removed through an instrument inserted through a 2.5–3.5 millimeter incision in the surface of the eye. According to the present invention, fragments which do not pass readily through the aspirating opening are dislodged.

In a first embodiment of the invention this is accomplished by providing some vibration of the instrument, for example, akin to the ultrasonic vibration which is provided during conventional phacoemulsification. The vibration may to some extent cause further fragmentation and also causes the fragment to move until it is positioned so it can pass through the aspirating opening.

According to a second embodiment of the invention, a paddle like member is pivotally mounted adjacent to the aspiration opening and biased to a position lying against the tube surface. Fragments which are lodged in the opening can be easily broken up by pivoting the paddle like member toward the opening, engaging the fragment and applying a force to the same which results in it being broken up. The smaller fragments resulting are then sucked through the aspirating opening. In this fashion, the fragments can be readily and easily removed from the eye.

Preferably the probe tube is provided with an interior portion supplying aspirating liquid, preferably water, through the end thereof and a sleeve extending about that portion having an aspirating opening adjacent the end thereof. Since the tube need not actually be inserted into the cloudy lens material, the end of the tube can be rounded, reducing the potential for damage to other tissue inherant in conventional phacoemulsification. Since the incision can be limited to 2.5–3.5 millimeters, less stitches are required to close it and less asigmatism results from healing which is substantially completed within two weeks.

Other purposes and invention will be clear from the following detailed description of the drawings.

DETAILED DESCRIPTION OF THE PREFERRED EMBODIMENT

Figure 1:
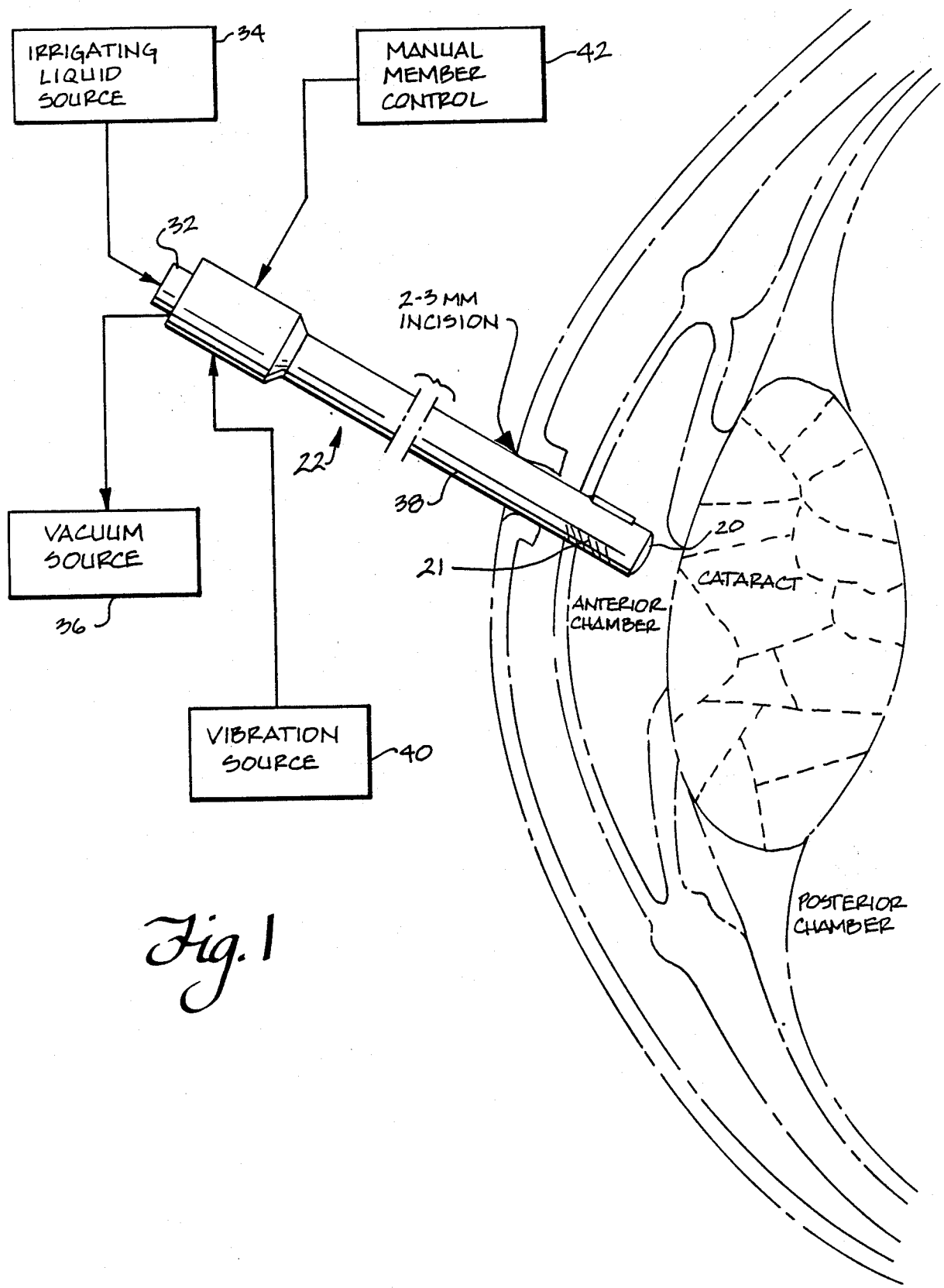
FIG. 1 shows a schematic view of the tissue extracting apparatus of the present invention in place within a schematically illustrated eye for removing cataract tissue.

Reference is now made to FIG. 1 which illustrates a first embodiment of the invention. The rounded end 20 of a probe tube 22 shown only partially in FIG. 1 has been inserted through a 2.5–3.5 millimeter incision conventionally made in the surface of the eye at an appropriate location. The end 20 of tube 22 is then manipulated adjacent to the cataract tissue which has already been softened and substantially fragmented by the previous application of laser radiation.

Figure 4:
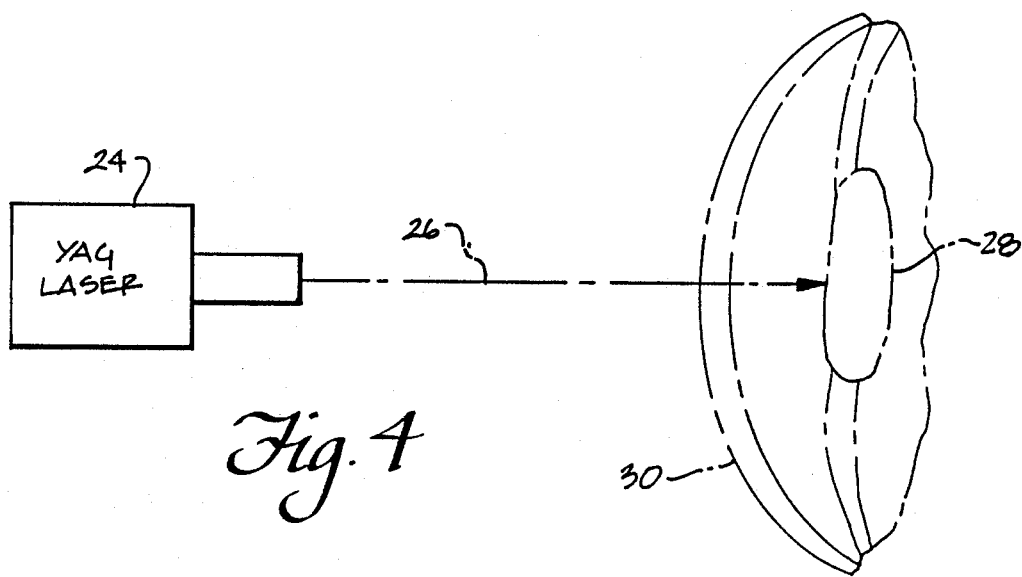
FIG. 4 shows a schematic view of the application of laser radiation from a YAG laser to soften the cataract tissue.

FIG. 4 shows a laser 24 schematically applying a beam of radiation 26 to a clouded lens 28 in a schematically illustrated eye 30. A conventional YAG laser using bursts of three mJ to five mJ focused on the center of the neucleus has been shown to produce satisfactory softening. At least 50 laser bursts are first applied to the posterior aspect of the nucleus at 3 mJ. Another 100–150 shots of 5–7 mJ are then applied to the center of the nucleus. Considerable time, a week or more, may pass between softening and removal.

Referring again to FIG. 1, irrigating liquid is supplied to the interior portion 32 of a rigid or semi-rigid tube 22 from a schematically illustrated irrigating liquid source 34. Tube 22 forms part of a probe which includes a handpiece (not shown) manipulated by the surgeon. The handpiece is essentially the same as a conventioned phacoemulsification device. Normally the irrigating liquid is sterile water. Vacuum from a suitable source 36 is similarly applied to a second portion 38 of tube 22 which is in the form of a sleeve extending about portion 32. Vibration source 40 and the manual control member 42 are also connected to tube 22. These various elements and sources can be arranged in much the same fashion as with conventional phacoemulsification devices available today.

Figure 2:
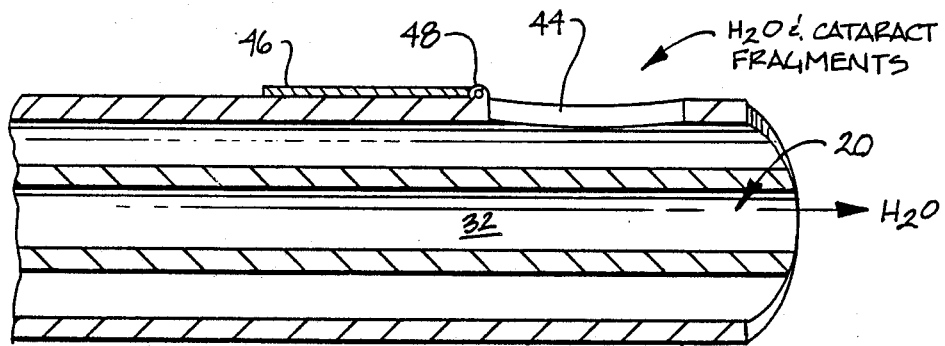
FIG. 2 shows a detailed view of the end of the tube of FIG. 1 showing the paddle like member overlying the aspirating opening.
Figure 3:
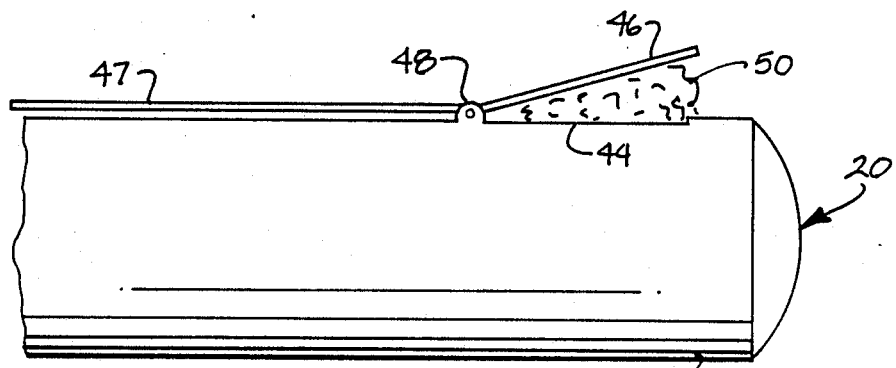
FIG. 3 shows a further schematic view illustrating a fragment of cataract tissue being broken up by a paddle like member.

FIGS. 2 and 3 show, in greater detail, the arrangement of the end 20 of one embodiment. As can be seen in FIG. 2, aspirating opening 44 is provided in the wall of tube 22 adjacent end 20. Aspirating liquid and cataract fragments are sucked through this opening into sleeve 38 and eventually returned to the vacuum source 36.

In order to dislodge fragments which do not readily pass through this opening, vibration source 40 can be used. The vibration is applied to an intensity and for a time until the surgeon observes the aspirating opening is no longer blocked.

In addition to, or as an alternative, a paddle like member 46 can be pivotally mounted at a pivot 48 adjacent the aspirating opening. Paddle like member 46 is normally biased into the position illustrated in FIG. 2 lying along the exterior surface of tube 22 during insertion of the instrument into the eye. From time to time fragments will become lodged in that opening as shown in FIG. 3. Those fragments may potentially be dislodged by use of the vibrations or alternatively may be broken up by use of the paddle like member. To do that, the paddle like member is simply moved by the manual control member with a cable or rod 47, for example, downward to engage the fragment, for example, fragment 50 and apply a force to the same, crushing the fragment between the surface of the tube 22 adjacent the opening and paddle like member 46. Very little force is, in fact, required to break up the very tiny and fragile fragments of tissue which are produced by the laser radiation. Once the fragment has been broken up, paddle like member 46 can be returned to its open position with cable or rod 47, for example, and the removal of the cataract tissue continued.

It is also conventional in this type of operation to polish the posterior chamber after removal of the clouded natural lens in order to make sure that all excessive cells are removed. It is convenient to provide a roughened portion 21 as shown in FIG. 1 on part of the wall of the tube 20 adjacent end 22 for that purpose.

Many changes and modifications in the above described embodiment of the invention can, of course, be made without departing from the scope of that invention. Accordingly, the scope is intended to be limited only by the scope of the appended claims.

What is claimed is:

1. An apparatus for extracting fragments of cataract tissue comprising:
   a probe with a tube having an aspirating opening and an irrigating opening at one end thereof adapted for insertion into the eye through an incision for supplying an irrigating liquid to the interior of said eye through said irrigating opening and aspirating that liquid and fragments of cataract tissue through said aspirating opening; and
   means for dislodging fragments of cataract tissue at said aspirating opening which have not passed through said aspirating opening including a member mounted on an exterior surface of said tube adjacent to said aspirating opening for controllable movement into contact with a fragment which has not passed through said aspirating opening for applying a force to the fragment to break up the fragment and means for moving said member into contact with the fragment, said means for dislodging fragments of cataract tissue further including means for vibrating said tube.

2. An apparatus as in claim 1 wherein said member is paddle shaped and pivotally mounted adjacent said aspirating opening so that pivotal movement of said member engages a fragment lodged in said aspirating opening to break up said fragment.

3. An apparatus as in claim 2 wherein said aspirating opening is through a wall of said tube adjacent the end thereof and includes means for normally biasing said member in an open position lying adjacent the exterior surface of said tube and said means for moving includes means manually operable outside the eye for causing pivoting of said member between said open position and a closed position to break up a fragment lodged in said aspirating opening.

4. An apparatus as in claim 1 wherein a portion of the wall of said tube adjacent said end is roughened for polishing the posterior capsule.

5. An apparatus as in claim 1 wherein said tube has an inner portion opening at the end for supplying said liquid and an outer sleeve extending about said inner portion and having at least one said aspirating opening in a wall thereof adjacent said end.

6. An apparatus as in claim 1 wherein the end of said tube is rounded.

7. An apparatus as in claim 1 further including means for supplying said liquid to a first portion of said tube and means for applying a vacuum to a second portion of said tube for aspiration.

8. A system for extracting a cataract comprising:
   a laser for producing laser radiation to soften said cataract; and an extracting device including a probe tube having an aspirating opening and an irrigating opening at one end thereof adapted for insertion into the eye through an incision and supplying an irrigation liquid to the interior of said eye through said irrigating opening and aspirating that liquid and fragments of cataract tissue through an aspirating opening, said probe tube including means for dislodging fragments of cataract tissue at said aspirating opening which have not passed through said aspirating opening including a member mounted adjacent to said aspirating opening for controllable movement into contact with a fragment which has not passed through said aspirating opening for applying a force to the fragment to break up that fragment and means for moving said member into contact with the fragment, said means for dislodging fragments of tissue further including means for vibrating said tube.

9. A system as in claim 10 wherein said member is paddle shaped and pivotally mounted adjacent said aspirating opening so that pivotal movement of said member engages a fragment lodged in said opening to break up said fragment.

10. A system as in claim 9 wherein said aspirating opening is through a wall of said tube adjacent an end thereof and includes means for normally biasing said member in an open position lying adjacent the exterior surface of said tube and said means for moving includes means manually operable outside the eye for causing pivoting of said member between said open position and a closed position to break up a fragment lodged in said aspirating opening.

11. A system as in claim 8 wherein a portion of the wall of said tube adjacent said end is roughened for polishing the posterior capsule.

12. A system as in claim 8 wherein said tube has an inner portion opening at an end for supplying said liquid and an outer sleeve extending about said inner portion and having at least one aspirating opening in a wall thereof adjacent said end.

13. A system as in claim 8 wherein the end of said tube is rounded.

14. A system as in claim 8 further including means for supplying said liquid to a first portion of said tube and means for applying a vacuum to a second portion of said tube for aspiration.

15. A system as in claim 8 wherein said laser is a YAG laser.

16. A method of extracting a cataract comprising the steps of:

focusing laser radiation onto said cataract to soften the same;

making an incision in the exterior surface of the eye;

inserting a tube through said incision to a position adjacent to said cataract;

supplying an irrigation liquid through a portion of said tube to said eye via an opening in said tube adjacent to a end thereof;

aspirating said liquid and fragments of cataract tissue through another portion of said tube via an aspirating opening adjacent said end; and dislodging fragments of cataract tissue at said aspirating opening which have not passed through said aspirating opening including manually causing a member pivotally mounted adjacent said aspirating opening to pivot into contact with a fragment which has not passed through said aspirating opening for applying a force to the fragment to break up that fragment.

17. A method as in claim 16 wherein said step of dislodging includes the step of vibrating said tube.

18. A method as in claim 16 including the step of polishing the posterior capsule with a roughened portion on a wall of said tube.

19. A method as in claim 16 wherein said step of making an incision includes making an incision no longer than 3.5 mm.

* * * * *